(12) United States Patent
Mizukoshi et al.

(10) Patent No.: US 7,070,567 B2
(45) Date of Patent: Jul. 4, 2006

(54) INFLATABLE CUFF FOR BLOOD PRESSURE MEASUREMENT

(75) Inventors: Toshiya Mizukoshi, Aichi-gun (JP); Hideo Nishibayashi, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 185 days.

(21) Appl. No.: 10/822,812

(22) Filed: Apr. 13, 2004

(65) Prior Publication Data

US 2005/0015015 A1 Jan. 20, 2005

(30) Foreign Application Priority Data

Apr. 21, 2003 (JP) .............................. 2003-116292

(51) Int. Cl.
*A61B 5/02* (2006.01)
(52) U.S. Cl. ...................................... 600/499; 600/490
(58) Field of Classification Search ..................... None
See application file for complete search history.

(56) References Cited

U.S. PATENT DOCUMENTS 4,920,971 A * 5/1990 Blessinger .................. 600/492
5,069,219 A * 12/1991 Knoblich .................... 600/492
5,388,585 A * 2/1995 Tomita ....................... 600/493
6,346,083 B1 2/2002 Nishibayashi et al.
6,497,668 B1 12/2002 Nishibayashi
6,969,356 B1 * 11/2005 Nishibayashi ............... 600/499

FOREIGN PATENT DOCUMENTS

JP A 5-269089 10/1993

* cited by examiner

*Primary Examiner*—Robert L. Nasser, Jr.
(74) *Attorney, Agent, or Firm*—Oliff & Berridge, PLC

(57) ABSTRACT

An inflatable cuff for blood pressure measurement includes a first inflatable bag to press an arterial vessel of a body portion of a living subject for stopping blood flow; a second inflatable bag for sensing a pulse wave propagating along the arterial vessel, which is supported by the inflatable cuff such that the second inflatable bag is located inside a downstream-side portion of the first inflatable bag in the direction of the blood flows; a shielding member disposed between the first inflatable bag and the second inflatable bag so as to prevent an oscillation of the first inflatable bag from propagating to the second inflatable bag; and a slidable separating member disposed between the shielding member and the second inflatable bag so as to prevent generation of a noise caused by a slide contact of the shielding member with the second inflatable bag.

13 Claims, 2 Drawing Sheets

[Fig. 1]
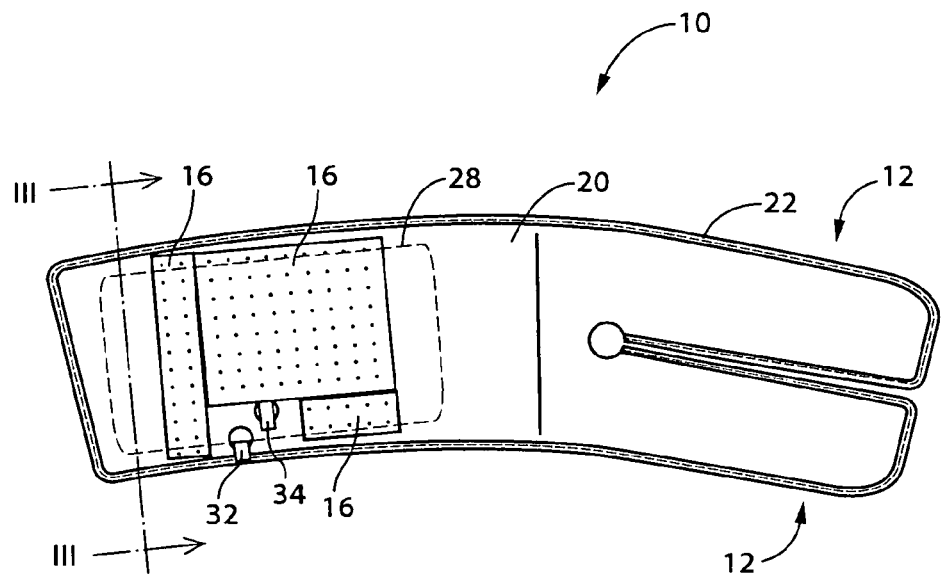
[Fig. 2]
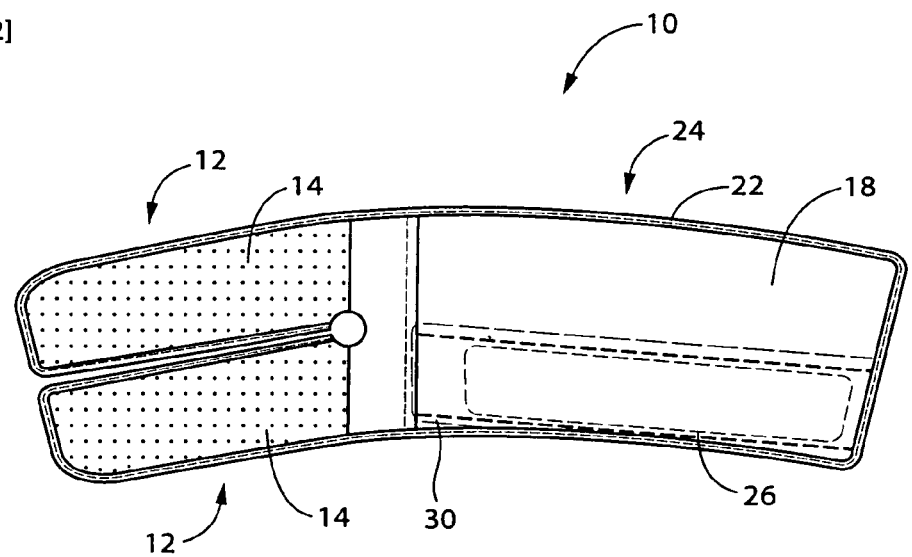
[Fig. 3]
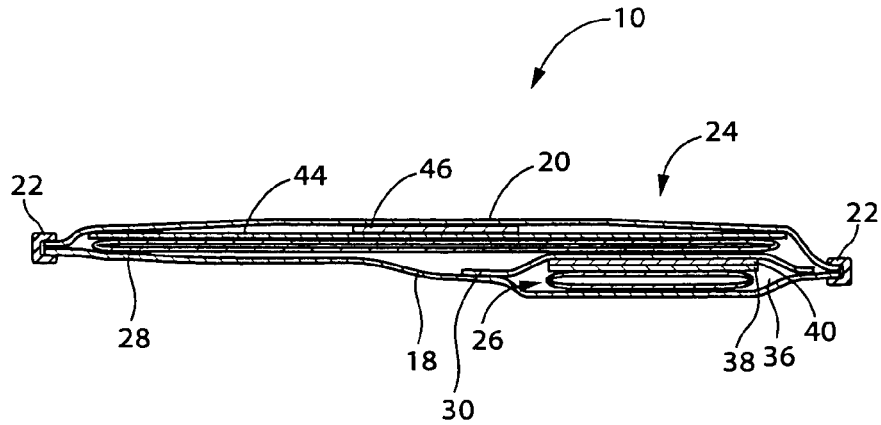

[Fig. 4]
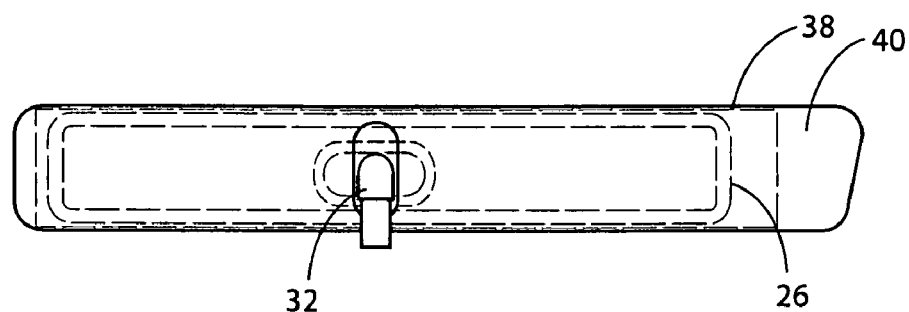
[Fig. 5]
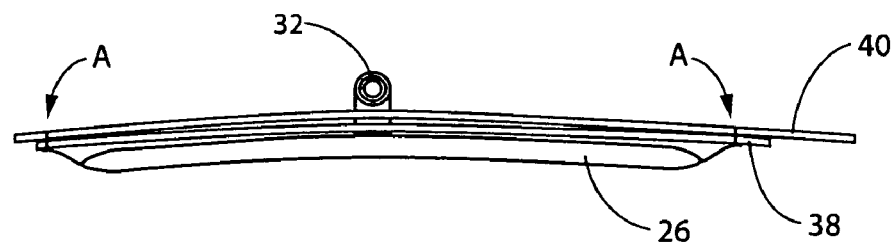

INFLATABLE CUFF FOR BLOOD PRESSURE MEASUREMENT

BACKGROUND OF THE INVENTION

1. Field of the Invention

The present invention relates to an inflatable cuff for oscillometric blood pressure measurement, which is adapted to be worn on a body portion of a living subject, and particularly to a cuff having a first inflatable bag for pressing the body portion and a second inflatable bag for sensing a pulse wave.

2. Description of Related Art

In general, an oscillometric blood pressure measuring device determines a blood pressure based on pulse waves continuously received by the cuff wound around a body portion during a slow deflation to reduce a pressure by the cuff.

The device adopts a static pressure of the inflatable bag as a systolic pressure, at a rising point of an envelope of amplitudes of the pulse waves, that is, a point where the amplitude of the pulse waves suddenly rises.

The device may determine an indefinite systolic pressure with an indefinite rising point of the envelope of the amplitudes of the pulse waves when the cuff has only one inflatable bag used both for pressing the body portion and for sensing the pulse wave. This is attributed to a propagation of pulsations, which are generated from an arterial vessel around an upstream end of the cuff to the cuff by an influence of the pulsations gradually increasing with the decreasing pressure of the cuff approaching the systolic pressure even when the pressure of the cuff is over the systolic pressure. The device tends to provide with the indefinite rising point of the envelope of the amplitudes of the pulse waves with the cuff wound, especially, around a portion where it is difficult to fully stop a blood flow in the arterial vessel by the cuff, such as an ankle.

To solve the above problem, JP 05-269089 A, U.S. Pat. Nos. 6,346,083 and 6,497,668 disclose a cuff having an inflatable bag for pressing a body portion so as to stop a flow of blood in an arterial vessel and an inflatable bag for sensing a pulse wave from the arterial vessel. The cuff disclosed in these references includes an outer bag for pressing the body portion and an inner bag for sensing the pulse wave. A device using this cuff provides with a relatively definite systolic pressure with a relatively definite rising point of the envelope of the amplitudes of the pulse waves sensed by the inner bag, because the inner bag is substantially located in the center of and on a body portion side of the outer bag and no pulsation directly propagates to the inner bag when the arterial vessel pulsates again around an upstream end of the outer bag.

To an outer side of the inner bag of the references, a shield plate is adhered so as to prevent oscillation of the outer bag from propagating to the inner bag. The shield plate causes the device to provide with a more definite systolic pressure preventing noises in the outer bag from propagating to the inner bag.

It is a disadvantage of the inventions disclosed in the references that noises produced by a relative slide motion of the shield plate and the bag for sensing the pulse waves, that is, by friction between the shield plate and the bag for sensing, cause inaccuracy in blood pressure measurement by propagating with signals output from the bag for sensing during slow deflation of the bag for pressing and the bag for sensing for blood pressure measurement because the shield plate is disposed outer side of the inner bag, that is, the bag for the pulse wave in the above references.

SUMMARY OF THE INVENTION

It is therefore an object of the present invention to provide an inflatable cuff for blood pressure measurement including an inflatable bag for pressing a body portion of a living subject and another inflatable bag for sensing a pulse wave, which is used for determining a definite blood pressure with reduced noises produced by friction.

To attain this object, the present invention provides the inflatable cuff for blood pressure measurement including: (1) a first inflatable bag which is inflatable to press an arterial vessel of a body portion of a living subject and stop flow of blood in the arterial vessel which the inflatable cuff is adapted to be wound around the body portion; (2) a second inflatable bag for sensing a pulse wave propagating along the arterial vessel, the second inflatable bag is supported by the inflatable cuff such that the second inflatable bag is located inside a dow steam-side portion of the first inflatable bag as seen in the direction in which the blood flows in the arterial vessel, and which has a dimension as measured in said direction that is smaller than a dimension of the first inflatable bag as measured in said direction; (3) a shielding member disposed between the first inflatable bag and the second inflatable bag so as to prevent an oscillation of the first inflatable bag from propagating to the second inflatable bag; and (4) a slidable separating member disposed between the shielding member and the second inflatable bag for preventing a slide contact of the shielding member with the second inflatable bag.

According to this feature of the present invention, the slidable separating member disposed between the shielding member and the second inflatable bag prevents the shielding member from contacting with the second inflatable bag, but the slidable separating member is in slide contact with the shielding member and with the second inflatable bag respectively, then the low friction of the slidable separating member reduces noises produced in blood pressure measurement by friction between the slidable separating member and the shielding member and between the slidable separating member and the second inflatable bag upon contact, on the grounds that friction coefficients between the slidable separating member and the shielding member and between the slidable separating member and the second inflatable bag are less than that between the shielding member and the second inflatable bag

BRIEF DESCRIPTION OF THE DRAWINGS

The above and optional objects, features, and advantages of the present invention will be better understood by reading the following detailed description of the exemplary embodiments of the invention when considered in conjunction with the accompanying drawings, wherein:

FIG. 1 illustrates an inflatable cuff for blood pressure measurement at an ankle in a plan view according to the present invention;

FIG. 2 illustrates the inflatable cuff for blood pressure measurement at the ankle in a bottom view;

FIG. 3 illustrates the inflatable cuff for blood pressure measurement in a sectional view taken along line 3—3 in FIG. 1

FIG. 4 illustrates a set of a second inflatable bag, a separating cloth and a shield plate in a plan view; and FIG. 5 illustrates the set of the second inflatable bag, a separating cloth and the shield plate in a front view.

DETAILED DESCRIPTION OF EXEMPLARY EMBODIMENTS

Hereinafter, there will be described an inflatable cuff for blood pressure measurement embodying the present invention, by reference to the drawings.

In FIG. 1, an inflatable cuff 10 which has a belt-like shape is about 14 cm in width and is slightly bent along a longitudinal direction to be formed an arch. The cuff 10 has two narrowed portions 12, 12 at one end in a longitudinal direction Each of the narrowed portions 12 is a half in width of the cuff 10 and has a fastener pad 14 on its inner surface, that is, a surface on a body portion side, and a main portion 70 of the cuff 10 also has fastener pads 16 on its outer surface, that is, a surface on the opposite side to the body portion side. The fastener pads 14 and 16 are fastened to each other, and the narrowed portions 12, 12 are unfastenably fixed to the main portion 70 at the fastener pads 14 and 16 with the cuff 10 wound around an ankle (not shown) and are on the most outside of the wound cuff 10. Consequently, the cuff 10 is fixed to the ankle.

A containing bag 24 consists of an inner cloth member 72 and an outer cloth member 20, both of which substantially are the same in shape as the cuff 10. The inner cloth member 72 and the outer cloth member 20 are mutually fixed by sewing with a circumferential cloth member 22. A portion of the inner cloth member 72 without the narrowed portions 12, 12 forms an inner cloth portion 18 which covers substantially from the center of the cuff 10 to the end opposite to the narrowed portion side in a longitudinal direction. A first inflatable bag 28 and a second inflatable bag 26 are in the containing bag 24.

As shown in FIG. 1, the first inflatable bag 28 for stopping the blood flow in the arterial vessel on the inner side of the cuff 10 has a rectangular shape. The bag 28 is slightly shorter in width than the containing bag 24, namely, than the cuff 10, and is also slightly shorter in length than the bag 24 in the longitudinal direction As shown in FIG. 2, the second inflatable bag 26 also has a substantially rectangular shape. The bag 26 is about between a third and a quarter in width of the bag 24, and is slightly shorter than the bag 24 in the longitudinal direction. The bags 28 and 26 are formed of soft resin sheet.

As shown in FIG. 1, the inflatable cuff 10 has a first conduit 34 integratedly connected to the first inflatable bag 28 and a second conduit 32 integratedly connected to the second inflatable bag 26. To ports of the conduits 34 and 32 protruding outside from the containing bag 24, pipes (not shown) are connected so as to supply air to the bags 28 and 26, respectively. The conduits 34 and 32 are connected each other through the pipe with a restriction.

As shown in FIGS. 2 and 3, the containing bag 24 includes a rectangular inner sheet 30 which has substantially the same length as the inner cloth portion 18 in the longitudinal direction and has approximately a half length of the inner cloth portion 18 in the transversal direction. The sheet 30 is disposed such that a long side of the sheet 30 on the downstream side of the blood flow in the arterial vessel when the cuff 10 is wound around the ankle is substantially located on a long side on the downstream side of the containing bag 24. Fixation of both of transversal edge portions of the sheet 30 to the inner cloth portion 18 provides with a cavity 36 which includes the second inflatable bag 26. The sheet 30 is formed of soft resin As shown in FIG. 3, on the outer side of the second inflatable bag 26 disposed a separating cloth 38 as a slidable separating member and on the outer side of the separating cloth 38, disposed a shield plate 40 as a shielding member. The lengths of the separating cloth 38 and of the shield plate 40 in a width-wise direction, that is, transversal direction in FIG. 3, are substantially equal to that of the second inflatable bag 26.

As shown in FIG. 4, the separating cloth 38 and the shield plate 40 have rectangular shapes whose long sides extend in the longitudinal direction. The separating cloth 38 has a surface of raised nylon cloth to contact with the shield plate 40 and the longitudinal length of the separating cloth 38 is a little longer than that of the second inflatable bag 26. The shield plate 40 is made of high-density polyethylene and the longitudinal length of the plate 40 is a little longer than that of the separating cloth 38 and the thickness of the plate 40 is 0.5 mm. The second inflatable bag 26, the separating cloth 38 and the shield plate 40 are integratedly fixed at respectively longitudinal ends, that is, at points A and A in FIG. 5, one another by sewing.

In FIG. 3, the containing bag 24 includes the first inflatable bag 28 on the outer side of the inner sheet 30, and a first support plate 44 and a second support plate 46 on the outer side of the bag 28. The plates 44 and 46 are formed of substantially hard material, such as hard resin, to support the cuff 10 to be a cylinder shape when wound around the ankle.

The shield plate 40 is employed for preventing pressure oscillation from propagating to the bag 26, which the pressure oscillation is generated in the bag 28 in synchronization with the pulse wave. The separating cloth 38 is employed for reducing fiction produced upon a relative slide motion of the bag 26 to the shield plate 40.

The inflatable cuff 10 operates as follows. When the cuff 10 is wound around an ankle (not shown) and the second inflatable bag 26 is positioned between the first inflatable bag 28 and the ankle. Then he bags 28 and 26 are supplied with air through the first conduit 32 and the second conduit 34 to reach the predetermined value, such as 250 mmHg, over a systolic blood pressure at the ankle, of an internal pressure of each of the bags 28 and 26, then the blood pressure measuring device (not shown) determines a blood pressure based on changes in the pulse wave amplitudes at the ankle with continuously sensing pressure oscillation, caused by pulse waves in the arterial vessel at the ankle, propagated to the bag 26 during slow deflation of each of the bags 28 and 26. Although the inflation and deflation of the bags 28 and 26 may cause the relative slide motion of the bag 26 to the plate 40, the low friction of the separating cloth 38 reduces noises produced upon the relative slide motion.

The separating cloth 38 disposed between the shield plate 40 and the bag 26 prevents the shield plate 40 from contacting with the bag 26, but the separating cloth 38 is in contact with the shield plate 40 and with the bag 26 respectively. The low friction of the separating cloth 38 reduces noises produced in blood pressure measurement by friction between the separating cloth 38 and the shield plate 40 and between the separating cloth 38 and the bag 26 upon contact, on the grounds that friction coefficients between the separating cloth 38 and the shield plate 40 and between the separating cloth 38 and the bag 26 are less than that between the shield plate 40 and the bag 26.

While the present invention has been described in its exemplary embodiment, the present invention may be otherwise embodied.

Instead of nylon cloth, the separating cloth 38 may be made of a fabric of natural fiber, such as hemp or cotton, or any kind of chemical fiber, or may be made of unwoven fabric.

And the separating cloth 38 may have another surface of a raised cloth to contact with the bag 26, or may have no surface of a raised cloth.

Instead of high-density polyethylene, the shield plate 40 as a shielding member may be made of polypropylene, polyester, polyethylene terephthalate or vinyl chloride. Or instead of the plate 40, the shielding member may be a bag filled with incompressible fluid such as liquid or gel.

It is to be understood that the present invention may be embodied with other changes, improvements, and modifications that may occur to a person skilled in the art without departing from the scope and spirit of the invention defined in the appended claims.

What is claimed is:

1. An inflatable cuff for blood pressure measurement, comprising:
    a first inflatable bag which is inflatable to press an arterial vessel of a body portion of a living subject and stop flow of blood in the arterial vessel which the inflatable cuff is adapted to be wound around the body portion;
    a second inflatable bag for sensing a pulse wave propagating along the arterial vessel, the second inflatable bag is supported by the inflatable cuff such that the second inflatable bag is located inside a downstream-side portion of the first inflatable bag as seen in the direction in which the blood flows in the arterial vessel, and which has a dimension as measured in said direction that is smaller than a dimension of the first inflatable bag as measured in said direction;
    a shielding member disposed between the first inflatable bag and the second inflatable bag so as to prevent an oscillation of the first inflatable bag from propagating to the second inflatable bag, and
    a slidable separating member disposed between the shielding member and the second inflatable bag for preventing a slide contact of the shielding member with the second inflatable bag.

2. An apparatus according to claim 1, wherein the slidable separating member is made of cloth.

3. An apparatus according to claim 2, wherein the slidable separating member is made of fabric of chemical fiber.

4. An apparatus according to claim 3, wherein the slidable separating member is made of fabric of nylon.

5. An apparatus according to claim 2, wherein the slidable separating member is made of fabric of natural fiber.

6. An apparatus according to claim 5, wherein the slidable separating member is made of fabric of hemp.

7. An apparatus according to claim 5, wherein the slidable separating member is made of fabric of cotton.

8. An apparatus according to claim 1, wherein the slidable separating member is made of unwoven fabric.

9. An apparatus according to claim 1, wherein the shielding member is made of hard resin.

10. An apparatus according to claim 9, wherein the resin is selected from the group of polyethylene, polypropylene, polyester, polyethylene terephthalate and vinyl chloride.

11. An apparatus according to claim 1, wherein the shielding member is a bag filled with incompressible fluid.

12. An apparatus according to claim 11, wherein the incompressible fluid is a liquid.

13. An apparatus according to claim 11, wherein the incompressible fluid is a gel.

* * * * *